United States Patent [19]

Tanaka et al.

[11] Patent Number: 5,710,308
[45] Date of Patent: Jan. 20, 1998

[54] PROCESS FOR PRODUCING OGRANOPHOSPHORUS ESTER COMPOUND AND REACTIVE FLAME RETARDANT

[75] Inventors: Keiji Tanaka; Munekazu Sataka, both of Kyoto,, Japan

[73] Assignee: Sanyo Chemical Industries, Ltd., Kyoto, Japan

[21] Appl. No.: 682,591

[22] PCT Filed: Jan. 25, 1995

[86] PCT No.: PCT/JP95/00081

§ 371 Date: Jul. 24, 1996

§ 102(e) Date: Jul. 24, 1996

[87] PCT Pub. No.: WO95/20593

PCT Pub. Date: Aug. 3, 1995

[30] Foreign Application Priority Data

Jan. 27, 1994 [JP] Japan ............... 6-026068

[51] Int. Cl.$^6$ ............... C07F 9/02; C07F 9/28
[52] U.S. Cl. ............... 558/97; 558/179; 562/817; 562/24; 562/819
[58] Field of Search ............... 558/97, 179; 562/817, 562/24, 819

[56] References Cited

U.S. PATENT DOCUMENTS

| | | | |
|---|---|---|---|
| 4,081,463 | 3/1978 | Birum et al. | 562/24 |
| 4,769,182 | 9/1988 | Hazen | 562/24 |
| 5,153,345 | 10/1992 | Knorr et al. | 558/98 |
| 5,153,346 | 10/1992 | Knorr | 558/98 |
| 5,334,760 | 8/1994 | Wachi et al. | 562/817 |

FOREIGN PATENT DOCUMENTS

| | | |
|---|---|---|
| 0 423 746 A1 | 4/1991 | European Pat. Off. . |
| 0 436 937 A1 | 7/1991 | European Pat. Off. . |

Primary Examiner—Joseph D. Anthony
Attorney, Agent, or Firm—Pollock, Vande Sande & Priddy

[57] ABSTRACT

① A process for producing a purified organophosphorus alkyl ester compound in which the reaction mixture obtained by reacting a dichlorophosphine derivative with (meth)acrylic acid is esterified with a lower monool, and the resulting reaction mixture is neutralized with an alkali metal hydroxide or alkaline earth metal hydroxide either in a solid form or in the form of an aqueous solution and purified; ② a process for producing a purified organophosphorus hydroxyalkyl ester compound or an alkylene glycol solution thereof which comprises subjecting the purified organophosphorus alkyl ester compound obtained by process ① to transesterification with an alkylene glycol; ③ a reactive flame retardant comprising the purified organophosphorus alkyl ester compound obtained by process ①; and ④ a reactive flame retardant comprising the purified organophosphorus hydroxyalkyl ester compound or alkylene glycol solution obtained by process ②.

16 Claims, No Drawings

5,710,308

PROCESS FOR PRODUCING OGRANOPHOSPHORUS ESTER COMPOUND AND REACTIVE FLAME RETARDANT

This application is a 371 of PCT/JP95/00081 filed Jan. 25, 1995

FIELD OF THE INVENTION

The present invention relates to a process for producing organophosphorus ester compounds and to reactive flame retardants comprising said compounds. More particularly, the invention relates to a process for producing purified organophosphorus ester compounds which can be used as a bifunctional comonomer for imparting flame resistancy to polyester resin or as an intermediate thereof and to reactive flame retardants.

BACKGROUND OF THE INVENTION

As reactive flame retardants for polyester resin and other purposes, organophosphorus ester compounds such as phosphinylcarboxylic acid esters, etc. have heretofore been employed. Such organophosphorus ester compounds may contain alkylene glycols and other contaminants that can be used in polyesterification, but should have been purified to remove other impurities that would interfere with resin formation.

As the production technology for providing purified organophosphorus ester compounds, there is known a process which comprises preparing a purified organophosphorus carboxylic acid compound in the first place and, then, esterifying it with a lower alcohol to provide a purified organophosphorus ester compound.

For the production of an organophosphorus carboxylic acid compound, the following processes ① and ②, among others, are known. In either process, a solid organophosphorus carboxylic acid compound is synthesized and the compound is then purified by rinsing with water. ①) A process for providing a purified compound which comprises reacting a dichlorophosphine derivative with (meth)acrylic acid in the presence of a catalyst such as an organic peroxide, hydrolyzing the reaction mixture, cooling the hydrolysate, and subjecting the resulting phosphinylcarboxylic acid crystals to filtration, aqueous rinse, and drying (for an improved yield, the filtrate is recrystallized) (U.S. Pat. No. 5,334,760).

② A process which comprises reacting dichloro(phenyl)phosphine with an excess of acrylic acid, hydrolyzing the reaction mixture, cooling the hydrolysate, and subjecting the precipitated 2-carboxyethyl(phenyl)phosphinic acid to aqueous rinse and drying (U.S. Pat. No. 4,081,463).

However, when a rinse-purified organophosphorus carboxylic acid compound is esterified and used as a reactive flame retardant for polyester resin, the polyester resin is stained black. The probable cause for this trouble is that the organophosphorus byproduct compound remaining in the rinse-purified organophosphorus carboxylic acid compound affects the esterification catalyst to stain the resin.

The purity of the rinse-purified compound can be increased by recrystallization. The check experiment performed by the inventors of the present invention also affirmed a decreased organophosphorus byproduct content of the recrystallized compound. When a purified ester was produced from a recrystallization-purified organophosphorus carboxylic acid compound and used in the production of polyester resin, too, the problem of stained polyester resin could be overcome. However, addition of a recrystallization step results in commercial disadvantages such as lowered yield, prolonged production time, increased labor, and increased cost and, therefore, improvements have been awaited.

Having been developed in the state of the art described above, the present invention has for its first object to provide a commercially useful process for producing a purified organophosphorus ester compound expediently and in high yield. The second object of the present invention is to provide a reactive flame retardant comprising a purified organophosphorus ester compound provided by said process, which is suitable for a comonomer of polyester resin and other applications.

SUMMARY OF THE INVENTION

The present invention provides the following production processes [1] and [2] for organophosphorus ester compounds and the following reactive flame retardants [3] and [4].

[1] Process for Producing an Organophosphorus Ester Compound

A process for producing an organophosphorus ester compound characterized in that ① a reaction mixture (M1) available on reaction of a dichlorophosphine derivative (a) of the general formula (1)

$R^1PCl_2$ (1)

[wherein $R^1$ represents a hydrocarbon group having 1 to 18 carbon atoms] with (meth)acrylic acid (b) is esterified with a monool having 1 to 4 carbon atoms (c) and 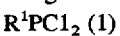 the resulting reaction mixture (M2) is neutralized with an alkali metal hydroxide or alkaline earth metal hydroxide (d) either in a solid form or in the form of an aqueous solution to provide ③ a purified organophosphorus alkyl ester compound (A) of the following general formula (2).

[wherein $R^1$ represents a hydrocarbon group having 1 to 18 carbon atoms; $R^2$ represents hydrogen or methyl; $R^3$ represents hydrogen or an alkyl having 1 to 4 carbon atoms; and $R^4$ represents an alkyl having 1 to 4 carbon atoms]

[2] Process for Producing an Organophosphorus Ester Compound

A process for producing an organophosphorus ester compound characterized in that ① the purified organophosphorus alkyl ester compound (A) obtained by process [1] is subjected to transesterification reaction with an alkylene glycol having 2 to 4 carbon atoms (e) to provide ② a purified organophosphorus hydroxyalkyl ester compound (B) of the following general formula (3), or a solution thereof in alkylene glycol (e).

[wherein $R^1$ represents a hydrocarbon group having 1 to 18 carbon atoms; $R^2$ represents hydrogen or methyl; $R^5$ represents hydrogen or a hydroxyalkyl group having 2 to 4 carbon atoms; $R^6$ represents a hydroxyalkyl group having 2 to 4 carbon atoms]

[3] Reactive Flame Retardant

A reactive flame retardant comprising a purified organophosphorus alkyl ester compound (A) as obtained by process [1], said (A) being a mixture of (A1) a monoalkyl ester compound of general formula (2) wherein $R^3$ represents hydrogen and (A2) a dialkyl ester compound of general formula (2) wherein $R^3$ represents an alkyl group having 1 to 4 carbon atoms.

[4] Reactive Flame Retardant

A reactive flame retardant comprising a purified organophosphorus hydroxyalkyl ester compound (B) or a solution thereof in an alkylene glycol (e) as obtained by process [2], said (B) being a mixture of (B1) a monohydroxyalkyl ester compound Of general formula (3) wherein $R^5$ represents hydrogen and (B2) a dihydroxyalkyl ester compound of general formula (3) wherein $R^5$ represents a hydroxyalkyl group having 2 to 4 carbon atoms, the molar ratio of (B1) to (B2) being 40:60 through 99:1.

The present invention comprising the above four aspects [1] to [4] has emerged from the results of the inventors' assiduous research for accomplishing the above-mentioned objects and on the basis of the consequent findings ① to ③, viz.

① When an alkyl ester is directly produced and purified from the reaction mixture following the reaction among a dichlorophosphine derivative, (meth)acrylic acid and monool, this alkyl ester is in liquid form and can be easily purified by alkali neutralization.

② Transesterification of the purified alkyl ester with an alkylene glycol readily yields a purified hydroxyalkyl ester with a minimum of impurity other than the starting alkylene glycol. The alkylene glycol not only functions as a solvent for the purified alkyl ester but can be utilized as part of a polyester production charge and, therefore, need not necessarily be removed.

③ The purified alkyl ester and the purified hydroxyalkyl ester and the alkylene glycol solution thereof can each be used advantageously as a reactive flame retardant for polyester resin and other purposes or as an intermediate thereof; viz.

1) Unlike the conventional purified ester available after aqueous rinse of the solid product and subsequent recrystallization, the above purified alkyl ester of the present invention is a compound made available in high yield by an expedient purification procedure comprising either phase separation of a liquid product or filtration. Nonetheless, the use of the purified alkyl ester as well as the purified hydroxyalkyl ester and alkylene glycol solution thereof in the production of polyester resin does not cause any appreciable coloration.

2) The reason for this freedom from resin coloration is probably attributable to a major difference in the residual amount of phosphorus-containing byproducts between the conventional purification procedure involving aqueous rinse of a solid compound and the purification according to the present invention which comprises neutralization and purification of a liquid compound.

3) Each of the alkyl ester and hydroxyalkyl ester is invariably a mixture of monoester and diester. As far as the monoester is concerned, there is an apprehension about the difference in the polyesterification reactivity with respect to two kinds of functional groups (alcoholic OH and OH bound to the P atom) but even the use of a mixture of monoester and diester allows the polyesterification reaction to proceed smoothly.

DETAILED DESCRIPTION

The process according to the first aspect [1] of the present invention comprises reacting a dichlorophosphine derivative (a) of general formula (1) with (meth)acrylic acid (b), esterifying the reaction mixture, and purifying the esterification mixture to give a purified organophosphorus alkyl ester compound (A) of general formula (2).

Referring to general formula (1), the hydrocarbon group having 1 to 18 carbon atoms $R^1$ includes but is not limited to an alkyl group having 1 to 18 carbon atoms and an aryl group having 6 to 18 carbon atoms. The alkyl group having 1 to 18 carbon atoms includes methyl, ethyl, propyl, butyl, octyl, dodecyl, and octadecyl, among others.

The aryl group having 6 to 18 carbon atoms includes phenyl, nonylphenyl, and dodecylphenyl, among others.

Preferred examples of $R^1$ are aryl group having 6 to 18 carbon atoms, with phenyl being most preferred.

(Meth)acrylic acid means acrylic acid or methacrylic acid.

The reaction between dichlorophosphine derivative (a) and (meth)acrylic acid (b) can be carried out with or without the aid of a catalyst such as an organic peroxide or an azonitrile compound but is preferably conducted in the absence of a catalyst because the reaction proceeds with good yield even without use of a catalyst. From the standpoint of reaction rate, the molar ratio of (a):(b) for use in the reaction is generally 1:1.01 to 1:1.5 and preferably 1:1.25 to 1:1.45.

In conducting the reaction between (a) and (b), it is optional to add (b) to (a) or (a) to (b), or even use a mixture of (a) and (b), but preferably (b) is added to (a).

The reaction temperature is generally 80° to 150° C. and preferably 90° to 120° C. The reaction time is generally 1 to 3 hours.

The resulting reaction mixture (M1) is considered to comprise the three kinds of product compounds represented by the following general formulas (4) to (6) and the unreacted residue of (meth)acrylic acid (b).

(4)

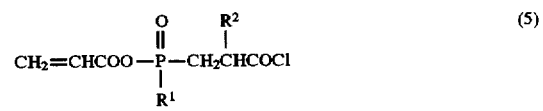

(5)

(6)

In each of the above formulas, $R^1$ represents a hydrocarbon group having 1 to 18 carbon atoms; and $R^2$ represents hydrogen or methyl.

The above reaction mixture (M1) is esterified with a monool having 1 to 4 carbon atoms (c) to give a reaction mixture .(M2). (M1) and (c) are generally reacted at 0° to 150° C. for 1 to 5 hours.

The monool having 1 to 4 carbon atoms (c) includes methanol, ethanol, n-propanol, i-propyl alcohol, n-butanol, t-butanol, etc. Among these monools, methanol or ethanol is preferred in view of the ease of removal after transesterification with an alkylene glycol. The amount of (c) for use with respect to (a) is generally not less than 2 molar equivalents and preferably in a range of 2 to 4 molar equivalents.

The reaction mixture (M2) contains the organophosphorus alkyl ester compound (A). This organophosphorus alkyl ester compound (A) in (M2) usually occurs as a mixture of the following monoalkyl ester compound (A1) and dialkyl ester compound (A2). The molar ratio of (A1) to (A2) in (M2) is generally in a range of 40:60 to 99:1. (A1) The monoalkyl ester compound of general formula (2) wherein $R^3$ is hydrogen (A2) The dialkyl ester compound of general formula (2) wherein R' is an alkyl group having 1 to 4 carbon atoms.

Taking phenyl as an example of $R^1$, the monoalkyl ester compound (A1) includes the monoesters of 3-[hydroxy(phenyl)phosphinyl]propionic acid with said monools such as methanol, ethanol, n-propanol, i-propyl alcohol, n-butanol, and t-butanol, typically methyl 3-[hydroxy(phenyl)phosphinyl]propionate, ethyl 3-[hydroxy(phenyl)phosphinyl]propionate, and so on.

Other specific examples of (A1) include the monoester compounds corresponding to those mentioned above in which an alkyl group having 1 to 18 carbon atoms or an aryl group having 6 to 18 carbon atoms (other than phenyl) has been substituted for said phenyl.

Taking phenyl again as an example of $R^1$, the dialkyl ester compound (A2) includes the diesters of 3-[hydroxy(phenyl)phosphinyl]propionic acid with said monools such as methanol, ethanol, n-propanol, i-propyl alcohol, n-butanol, and t-butanol, typically methyl 3-[methoxy(phenyl)phosphinyl]propionate, ethyl 3-[ethoxy(phenyl)phosphinyl]propionate, and so on.

Other specific examples of (A2) include the diester compounds corresponding to the compounds mentioned just above in which an alkyl group having 1 to 18 carbon atoms or an aryl group having 6 to 18 carbon atoms (other than phenyl) has been substituted for said phenyl.

The reaction mixture (M2) is neutralized with an alkali metal hydroxide or alkaline earth metal hydroxide (d) either in solid form or in the form of an aqueous solution, and then purified to provide a purified compound (A). As examples of (d), sodium hydroxide, potassium hydroxide, magnesium hydroxide, calcium hydroxide, etc. can be mentioned, although alkali metal hydroxides are preferred.

When the reaction mixture (M2) is to be neutralized with a solid form of (d), (M2) is mixed with solid (d) and the precipitated salt is harvested by filtration.

When (d) is used in the form of an aqueous solution, an aqueous solution of (d) is mixed with (M2) and, then, the mixture is purified by phase separation. The use of an aqueous solution of (d) is preferred in view of the relative ease of purification.

The amount of (d) can be based on the theoretical amount needed for the neutralization of byproduct hydrochloric acid and the unreacted residue of the starting material (meth)acrylic acid (b) in the reaction mixture (M2). Thus, the equivalent ratio of [hydrochloric acid in (M2)+unreacted (b) in (M2)]/(d) in a range of 1/(0.8 to 1) and preferably 1/(0.95 to 1) can be employed. If the proportion of (d) exceeds the above range, the yield will be lowered, while the use of (d) in a proportion below said range results in decreased purity.

The purified product of (A) which can be obtained by the process [1] of the invention is usually a mixture of (A1) and (A2) in a molar ratio of 40:60 through 99:1.

This purified product of (A) is lean in the byproduct phosphinic acid derivative originating from the starting dichlorophosphine derivative (for example, phenylphosphinic acid is byproduced when the starting material is dichlorophenylphosphine). Thus, in the process [1] of the present invention, the molar ratio of (A) to said byproduct phosphinic acid derivative can be increased generally to $\geq 99.85$: $\leq 0.15$ and preferably to $\geq 99.9$: $\leq 0.10$.

Since the byproduct phosphinic acid derivative has been removed to the above level, the purified product of (A) obtained by process [1] and the purified product of (B) or alkylene glycol (e) solution thereof as obtained by process [2] using the purified product of (A) as an intermediate starting material present only a low risk of resin staining when used in the production of a polyester.

In accordance with process [1] of the invention, barring an excessive loss in the phase separation step or the filtration step, the yield of the purified product of (A) can be usually maintained at a high level of not less than 95%.

Process [2] of the present invention is the process in which the purified product of (A) obtained by process [1] is subjected to transesterification reaction with an alkylene glycol having 2 to 4 carbon atoms (e) to provide a purified organophosphorus hydroxyalkyl ester (B) or a solution thereof in the alkylene glycol (e).

While the alkylene glycol having 2 to 4 carbon atoms includes ethylene glycol, propylene glycol and butylene glycol, ethylene glycol is preferred in view of its availability and usability of the (e) solution in polyester production without removal of the unreacted starting material.

The amount of (e) for use in the transesterification reaction with respect to (A) is generally 1 to 20 molar equivalents and preferably 2 to 10 molar equivalents. Depending on the proportion of (e) in relation to (A), either a purified product of (B) or a solution thereof in the alkylene glycol (e) is obtained and, in the case of the latter, the concentration of the the solution is variable.

Where necessary, a catalyst may be added for promoting the transesterification reaction between (A) and (e). The catalyst that can be used includes tin series catalysts such as dibutyltin oxide etc., acid catalysts such as hydrochloric acid, sulfuric acid, heteropolyacids, etc., amine catalysts such as triethylamine, diazabicycloundecene, etc., or mixtures thereof. Preferred are tin series catalysts. The amount of the catalyst with respect to (A) is generally 5 weight % or less and preferably 0.01 to 5 weight %.

The transesterification reaction temperature is generally 50° to 220° C and preferably 60° to 150° C. The reaction can be carried out at superatmospheric, atmospheric or subatmospheric pressure. The reaction end-point can be checked by gas chromatographic analysis. Following the reaction, the excess (e) can be removed by the routine procedure to provide a purified product of (B). The solution in (e) can also be directly used as a reactive flame retardant.

(B) may occur as a mixture of the following monohydroxyalkyl ester compound (B1) and dihydroxyalkyl ester compound (B2).

(B1) The monohydroxyalkyl ester compound of general formula (3) wherein R' represents hydrogen (B2) The dihydroxyalkyl ester compound of general formula (3) wherein $R^5$ represents a hydroxyalkyl group having 2 to 4 carbon atoms.

As representative examples of (B1), hydroxyethyl, hydroxypropyl and hydroxybutyl esters of 3-[hydroxy(phenyl)phosphinyl]propionic acid can be mentioned. In addition, there can be mentioned the compounds corresponding to those mentioned for (A1) in which the alkyl group of the monoalkyl ester of (A1) has been replaced with a hydroxyalkyl group such as those mentioned just above.

As representative examples of (B2), there can be mentioned hydroxyethyl 3-[hydroxyethoxy(phenyl)phosphinyl] propionate, hydroxypropyl 3-[hydroxypropoxy(phenyl) phosphinyl]propionate, and hydroxybutyl 3-[hydroxybutoxy(phenyl)phosphinyl]propionate can be mentioned. In addition, there can be mentioned the compounds corresponding to those mentioned for (A2) which have been di-esterified by ethylene glycol, propylene glycol or butylene glycol.

The organophosphorus hydroxyalkyl ester compound (B) produced by process [2] is generally a mixture of (B1) and (B2) in a molar ratio of 40:60 through 99:1.

The reactive flame retardant according to the aspect [3] of the present invention is a reactive flame retardant comprising a purified organophosphorus alkyl ester compound (A) as obtained by the process [1] of the present invention, said (A) being a mixture of monoalkyl ester compound (A1) and dialkyl ester compound (A2).

The reactive flame retardant according to the aspect [4] of the present invention is a reactive flame retardant comprising a purified organophosphorus hydroxyalkyl ester compound (B) or a solution thereof in an alkylene glycol as obtained by the process [2] of the present invention, said (B) being a mixture of monohydroxyalkyl ester compound (B1) and dihydroxyalkyl ester compound (B2) in a molar ratio of 40:60 through 99:1.

The reactive flame retardant according to the aspect [3] of the present invention is different from the reactive flame retardant according to aspect [4] in that whereas the ester in aspect [3] is an alkyl ester, the ester in aspect [4] is a hydroxyalkyl ester.

When the alkyl ester is used as part of the charge for polyester production, it is built into the polyester as the transesterification and polyesterification reactions are properly conducted. Therefore, the reactive flame retardant according to aspect [3] of the present invention can be used not only a synthetic intermediate for the reactive flame retardant according to aspect [4] of the invention but also as a reactive flame retardant for polyester resin just as is the reactive flame retardant according to aspect [4].

In the reactive flame retardant according to the aspect [4] of the present invention, the molar ratio of (B1) to (B2) is generally 40:60 through 99:1 and preferably 50:50 through 97:3.

The reactive flame retardants according to the aspects [3] and [4] of the present invention may contain said alkylene glycol (e). The concentration of (e) is not so critical and may be chosen from a range taking into consideration the amount of the alcohol component required for the production of a polyester.

The component (e) serves not only as a diluent (solvent) for phosphorus-containing compounds (A) and (B) but also as a polyester component.

Each of the reactive flame retardants according to the aspects [3] and [4] of the present invention is of value as a comonomer unit of polyester resin for various applications such as polyester fiber, polyester film, unsaturated polyester molding compounds, alkyd coatings, and so on.

Thus, in producing a polyester by copolymerizing an acid component such as dimethyl terephthalate with an alcohol component such as ethylene glycol, a flame-retarded polyester can be obtained by using the reactive flame retardant according to aspect [3] and/or aspect [4] of the invention as a component of the charge.

The proportion of the reactive flame retardant [3] or [4] of the present invention in terms of atomic phosphorous relative to the polyester resin is generally 0.1 to 5 weight % and preferably 0.3 to 2.5 weight %. If the proportion is less than 0.1 weight %, no sufficient flame retardancy will be obtained. If the limit of 5 weight % is exceeded, the mechanical strength of the polyester will be sacrificed.

Regarding the production technology for flame-retardant polyester resin, e.g. for the production of fibers, the process described in U.S. Pat. No. 4,033,936 can be employed except that the reactive flame retardant according to aspect [3] or [4] of the present invention is used in lieu of the phosphinic acid derivative used in the process of the above-mentioned patent.

EXAMPLES

The following examples describe the present invention in further detail and should by no means be interpretated as defining the scope of the invention.

Example 1

① A 200 ml-glass reaction vessel equipped with a stirrer was charged with 35.80 g of dichlorophenylphosphine. Then, 20.90 g of acrylic acid was added dropwise over 30 minutes at 90° to 110° C. to provide a reaction mixture (M1-1). To this reaction mixture (M1-1) was added 16.34 g of methanol dropwise at 20° C. and the mixture was refluxed at 60° C. for 3 hours. The excess methanol and acrylic acid were then distilled off at 85° C. and 10 mmHg to provide a reaction mixture (M2-1).

② The above reaction mixture (M2-1) was washed with 15% aqueous sodium hydroxide solution, using the latter in a volume corresponding to one equivalent with respect to the residual acrylic acid, byproduct hydrochloric acid, and byproduct phenylphosphinic acid in reaction mixture (M2-1) and allowed to stand for phase separation.

③ As the product after this purification, 47.06 g of a purified mixture (A-1a) of the following compounds (A1—1) and (A2-1) was obtained.

(A1-1) Methyl 3-[hydroxy(phenyl)phosphinyl]propionate
(A2-1) Methyl 3-[methoxy(phenyl)phosphinyl]propionate This purified mixture (A-1a) was analyzed by $^1$H-NMR and $^{13}$C-NMR spectrometry. As determined from the area ratios of the respective signals on the $^1$H-NMR spectrum, the molar ratio of (A1-1)/(A2-1)/byproduct phenylphosphinic acid was 49.97/49.95/0.08. All the other components were traces below the detection limit. Moreover, as calculated from the area ratio of the respective signals on the $^1$H-NMR spectrum, the reaction rate based on the starting dichlorophenylphosphine was 97.0%.

Example 2

Except that 37.76 g of n-butanol was used in lieu of 16.34 g of methanol and the reflux temperature of 130° C. was used, the procedure of Example 1 was otherwise repeated to provide 59.67 g of a purified mixture (A-2) of the following compounds (A1-2) and (A2—2).

(A1-2) Butyl 3-[hydroxy(phenyl)phosphinyl]propionate
(A2—2) Butyl 3-[butoxy(phenyl)phosphinyl]propionate This purified mixture (A-2) was analyzed by the same method as in Example 1. The molar ratio of (A1—2) to (A2—2) was approximately 1:1. The reaction rate, also determined as in Example 1, was 97.0%.

Example 3

A 200 ml-glass reaction vessel equipped with a stirrer was charged with 47.06 g of the purified mixture (A-1a) obtained in Example 1 and 74.64 g of ethylene glycol, and the temperature was increased gradually from room. temperature to 100° C. under constant agitation at a reduced pressure of 20 mmHg. The mixture was further stirred at 100° to 105° C. for 2.5 hours, with the byproduct methanol being removed from the system. This transesterification reaction yielded 112.10 g of an ethylene glycol solution containing a mixture (B-1a) of the following compounds (B1—1) and (B2-1).

(B1—1) Hydroxyethyl 31[hydroxy(phenyl)phosphinyl] propionate (B2-1) Hydroxyethyl 3-[hydroxyethoxy(phenyl) phosphinyl]-propionate (B1—1) and (B2-1) in the above mixture (B-1a) were indentified by $^1$H-NMR and $^{13}$C-NMR spectrometry. From the area ratio of the respective signals on the $^1$H-NMR spectrum, the molar ratio of (B1—1) to (B2-1) was found to be approximately 1:1. As calculated from the area ratio of the signals on the $^1$H-NMR, the reaction rate based on the starting mixture (A-1a) was 98.0%.

Example 4

Except that 59.67 g of the purified mixture (A-2) obtained in Example 2 was 7used, the procedure of Example 3 was otherwise repeated to provide 112.10 g of an ethylene glycol solution containing a mixture (B-2) of the following compounds (B1-2) and (B2—2).

(B1-2) Hydroxyethyl 3-[hydroxy(phenyl)phosphinyl] propionate (B2—2) Hydroxyethyl 3-[hydroxyethoxy (phenyl)phosphinyl]-propionate (B1-2) and (B2—2) in the above mixture (B-2) were identified as in Example 3 and it was also confirmed that (B1-2) and (B2—2) occurred in a molar ratio of approximately 1:1. The reaction rate based on the starting mixture (A-2) was 97.0%.

Example 5

Except that methanol was added at 40° C. instead of 20° C., the procedure of Example 1 was otherwise repeated to provide 45.8 g of a purified mixture (A-1b) of (A1—1) and (A2-1).

(A1—1) and (A2-1) in the above purified mixture (A-1b) were identified by $^1$H-NMR and $^{13}$C-NMR spectrometry. From the area ratio of the respective signals on the $^1$H-NMR spectrum, it was confirmed that (A1—1) and (A2-1) had formed in a molar ratio of approximately 8:2. Based on the area ratio of the respective signals on the $^1$H-NMR spectrum, the reaction rate was calculated to be 97.0% relative to the starting dichlorophenylphosphine.

Example 6

Except that the purified mixture (A-1b) obtained in Example 5 was used in lieu of the purified mixture (A-1a) obtained in Example 1, the procedure of Example 3 was otherwise repeated to provide 111.10 g of an ethylene glycol solution containing a purified mixture (B-1b) of (B1—1) and (B2-1).

(B1—1) and (B2-1) in the above purified mixture (B-1b) were identified by $^1$H-NMR and $^{13}$C-NMR spectrometry, and from the area ratio of the respective signals on the $^1$H-NMR spectrum, it was confirmed that (B1—1) and (B2-1) were present in a molar ratio of approximately 8:2. The reaction rate calculated from the area ratio of the respective signals on the $^1$H-NMR spectrum was 98.5% based on the starting mixture (A-1b).

Comparative Example 1

Except that 9.18 g of water was used in lieu of 16.34 g of methanol, the procedure of Example 1 was otherwise repeated. However, in the purification step using aqueous sodium hydroxide solution, the mixture became a homogeneous system which prevented phase separation.

Comparative Example 2

Using 501.2 g of dichlorophenylphosphine, 3.2 g of t-butyl peroxybenzoate, 201.8 g of acrylic acid, and 0.92 L of water, a rinse-purified 3-[hydroxy(phenyl)phosphinyl] propionic acid was prepared by the procedure described in U.S. Pat. No. 5,334,760, namely the steps of hydrolyzing the reaction mixture after completion of the reaction, cooling it, harvesting the resulting crystals by filtration, rinsing the crystal crop with water, and drying it. The yield was 564.9 g or 94.2%. From the area ratio of the respective signals on the $^1$H-NMR spectrum, the molar ratio of 3-[hydroxy (phenyl)phosphinyl]propionic acid to phenylphosphinic acid was found to be 99.10:0.9. The other components were traces below the detection limit.

Comparative Example 3

In 500 ml of water at 80° C. was dissolved 149.8 g of the rinse-purified 3-[hydroxy(phenyl)phosphinyl]propionic acid obtained in Comparative Example 2 to prepare an aqueous solution. This aqueous solution was cooled to 10° C. and the resulting crystals were harvested by filtration, rinsed with water, and dried in a vacuum dryer at 60° C. to provide 111.3 g of a recrystallization-purified 3-[hydroxy(phenyl) phosphinyl]propionic acid. The recrystallization yield was 74.3% and the yield based on the starting dichlorophenylphosphine was 94.2% (yield of rinse-purified product)× 74.3% (recrystallization yield)=69.8%.

Example 7

A reactor was charged with 40 parts of terephthalic acid, 10 parts of isophthalic acid, and 25 parts of ethylene glycol, and the dehydrative esterification reaction was carried out at 220° C. and 0.5 kg/cm².

Then, 0.34 part of lithium acetate, 0.015 part of antimony trioxide, 0.005 part of phosphoric acid, and 13 parts of an ethylene glycol solution of the mixture (B-1a) obtained in Example 3 were added and the polymerization reaction was carried out at 260° C. in a vacuum of 2 mmHg for 2.5 hours to provide 63 parts of polyester resin (P-1).

This polyester resin (P-1) was colorless and transparent, had a Tg of 51° C., and showed an intrinsic viscosity of 0.386 (20° C.) when dissolved in 1,2-dichloroethane-phenol (1:1, w/w).

Example 8

Except that 10 parts of an ethylene glycol solution of mixture (B-1b) was used in lieu of 10 parts of an ethylene glycol solution of mixture (B-1a), the procedure of Example 7 was otherwise repeated to provide 63 parts of polyester resin (P-2). This polyester resin (P-2) was colorless and transparent, had a Tg of 53° C., and an intrinsic viscosity of 0.371 (20° C.).

Comparative Example 4

A glass reaction vessel was charged with 49.92 g of the rinse-purified 3-[hydroxy(phenyl)phosphinyl]propionatic acid obtained in Comparative Example 2 and 74.64 g of ethylene glycol and the temperature was increased gradually from room temperature to 100° C. in a vacuum of 20 mmHg, with constant stirring. The mixture was further stirred at 100° to 105° C. for 2.5 hours to carry out the esterification reaction with constant removal of water from the reaction system to provide 102.80 g of an ethylene glycol solution of hydroxyethyl 3-[hydroxy(phenyl)phosphinyl]propionate.

Then, using 13 parts of the above ethylene glycol solution of hydroxyethyl 3-[hydroxy(phenyl)phosphinyl]propionate in lieu of 13 parts of the ethylene glycol solution of mixture (B-1a), the procedure of Example 7 was otherwise repeated to provide 63 parts of polyester resin (P-3). This polyester (P-3) was black and showed a Tg of 50° C.

Reference Example 1

Except that the recrystallization-purified 3-[hydroxy (phenyl)phosphinyl]propionic acid obtained in Comparative Example 3 was used in lieu of the rinse-purified 3-[hydroxy (phenyl)phosphinyl]propionic acid, the procedure of Comparative Example 4 was repeated to provide 102.81 g of an ethylene glycol solution of hydroxyethyl 3-[hydroxy (phenyl)phosphinyl]propionate.

In addition, using 13 parts of this ethylene glycol solution of hydroxyethyl 3-[hydroxy(phenyl)phosphinyl]propionate, the procedure of Example 7 was repeated to provide 63 parts of polyester resin (P-4). This polyester resin (P-4) was colorless and transparent and showed a Tg of 52° C.

INDUSTRIAL APPLICABILITY

As described above, purified organophosphorus ester compounds can be produced by the process of the present invention in an expedient manner and in high yield; viz.

(1) In the process of the invention, an alkyl ester is directly produced from a reaction mixture after completion of the reaction between a dichlorophosphine derivative and (meth)acrylic acid and because this alkyl ester is a liquid, it can be easily purified by phase separation or filtration after alkali neutralization and the yield is high compared with purification by the rinse and recrystallization process. Thus, the process is commercially advantageous.

(2) Moreover, from the purified alkyl ester, a high-purity hydroxyalkyl ester or a solution thereof in the alkylene glycol, lean in contaminant compounds other than the starting alkylene glycol, can be easily produced by transesterification. Since the alkylene glycol can be utilized as part of the charge for polyester production, it need not necessarily be removed.

(3) These purified alkyl ester and hydroxyalkyl ester do not present the resin coloration problem, despite the fact that they are obtained by the expedient purification procedure, namely phase separation of a liquid compound or filtration.

The purified alkyl ester and the purified hydroxyalkyl ester and its alkylene glycol solution, which can be used as the reaction flame retardants of the present invention, are obtained by the process having the above-mentioned advantageous features (1) to (3). Moreover, each of said alkyl ester and hydroxyalkyl ester is a mixture of monoester and diester, but the polyesterification reaction can be conducted smoothly even when the mixture is used as a comonomer unit of polyester resin.

Therefore, the reactive flame retardant comprising the purified organophosphorus ester compound or an alkylene glycol solution thereof as provided by the process of the present invention can be advantageously used as a comonomer for imparting flame retardancy to polyester resin.

Thus, when the reactive flame retardant of the invention is used as a comonomer unit for the production of polyester resin, not only high flame retardancy is imparted to the resin but a polyester resin of high molecular weight with a higher glass transition temperature (Tg) can be easily obtained.

We claim:

1. A process for producing an organophosphorus ester compound characterized in that ① a reaction mixture (M1) is produced by reaction of a dichlorophosphine derivative (a) of the general formula (1): R¹PCl₂ (1)

wherein R¹ represents a hydrocarbon group having 1 to 18 carbon atoms with (meth) acrylic acid (b) said reaction is conducted in the absence of a catalyst and subsequently is esterified with a monool having 1 to 4 carbon atoms (c) to produce a reaction mixture (M2)

② the resulting reaction mixture (M2) is neutralized with an alkali metal hydroxide or alkaline earth metal hydroxide (d) either in a solid form or in the form of an aqueous solution, wherein (d) is used in an amount corresponding to an equivalent ratio of hydrochloric acid in (M2)+unreacted (b) in (M2)/(d) in a range of 1/(0.8 to 1), and purified by phase separation or filtration to provide ③ a purified organophosphorus alkyl ester compound (A) of the following general formula (2).

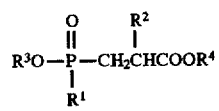

(2)

wherein R¹ represents a hydrocarbon group having 1 to 18 carbon atoms; R² represents hydrogen or methyl; R³ represents hydrogen or an alkyl group having 1 to 4 carbon atoms; R⁴ represents an alkyl group having 1 to 4 carbon atoms.

2. The process for producing an organophosphorus ester compound according to claim 1 wherein R¹ is an aryl group having 6 to 18 carbon atoms.

3. The process for producing an organophosphorus ester compound according to claim 1 wherein a purified organophosphorus alkyl ester compound (A) is a mixture of (A1) a monoalkyl ester compound of general formula (2) wherein R³ represents hydrogen and (A2) a dialkyl ester compound of general formula (2) wherein R³ represents an alkyl group having 1 to 4 carbon atoms.

4. The process of claim 1 wherein R³ represents an alkyl group having 1 to 4 carbon atoms.

5. The process of claim 1 wherein R¹ is selected from the group consisting of methyl, ethyl, propyl, butyl, octyl, dodecyl, octadecyl, phenyl, nonylphenyl, and dodecylphenyl.

6. The process of claim 1 wherein R¹ is phenyl.

7. The process of claim 1 wherein the molar ratio of (a):(b) is 1:1.01 to 1:1.5.

8. The process of claim 1 wherein the molar ratio of (a):(b) is 1:1.25 to 1:1.45.

9. The process of claim 1 wherein said reaction is carried out at a temperature of 80°–150° C.

10. The process of claim 1 wherein said reaction is carried out at a temperature of 90°–120° C.

11. The process of claim 1 wherein said monool is methanol or ethanol.

12. The process of claim 1 wherein the amount of (c) based upon the amount of (a) is at least 2 molar equivalents.

13. The process of claim 12 wherein the amount of (c) based upon the amount of (a) is 2 to 4 molar equivalents.

14. A process for producing an organophosphorus ester compound characterized in that ① the purified organophosphorus alkyl ester/compound (A) obtained by the process according to claim 1 is subjected to transesterification reaction with an alkylene glycol having to 4 carbon atoms (e) to provide ② a purified organophosphorus hydroxyalkyl ester compound (B) of the following general formula (3) or a solution thereof in alkylene glycol (e),

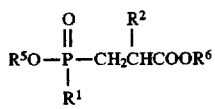  (3)

wherein $R^1$ represents a hydrocarbon group having 1 to 18 carbon atoms; $R^2$ represents hydrogen or methyl; $R^5$ represents hydrogen or a hydroxyalkyl group having 2 to 4 carbon atoms; $R^6$ represents a hydroxyalkyl group having 2 to 4 carbon atoms.

15. The process for producing an organophosphorus ester compound according to claim 14 wherein $R^1$ is an aryl group having 6 to 18 carbon atoms.

16. The process for producing an organophosphorus ester compound according to claim 14 wherein a purified organophosphorus hydroxyalkyl ester compound (B) is a mixture of (B1) a monohydroxyalkyl ester compound of general formula (3) wherein $R^5$ represents hydrogen and (B2) a dihydroxyalkyl ester compound of general formula (3) wherein $R^5$ represents a hydroxyalkyl group having 2 to 4 carbon atoms, the molar ratio of (B1) to (B2) being 40:60 to 99:1.

* * * * *

UNITED STATES PATENT AND TRADEMARK OFFICE
CERTIFICATE OF CORRECTION

PATENT NO. : 5,710,308
DATED : January 20, 1998
INVENTOR(S) : Tanaka, et. al.

It is certified that error appears in the above-identified patent and that said Letters Patent is hereby corrected as shown below:

Title page, item [54] and col. 1, the title should read-- Process for Producing Organophosphorus Ester Compound and Reactive Flame Retardant--.

Title page, item [75], Inventors: should read --Keiji Tanaka; Munekazu Satake, both of Kyoto, Japan--

Signed and Sealed this

Second Day of June, 1998

Attest:

BRUCE LEHMAN

*Attesting Officer*  *Commissioner of Patents and Trademarks*